(12) United States Patent
Richael

(10) Patent No.: US 7,923,600 B2
(45) Date of Patent: Apr. 12, 2011

(54) GENERATION OF MARKER-FREE AND BACKBONE-FREE TRANSGENIC PLANTS USING A SINGLE BINARY APPROACH

(75) Inventor: Craig Richael, Meridian, ID (US)

(73) Assignee: J.R. Simplot Company, Boise, ID (US)

( * ) Notice: Subject to any disclaimer, the term of this patent is extended or adjusted under 35 U.S.C. 154(b) by 992 days.

(21) Appl. No.: 11/701,528

(22) Filed: Feb. 2, 2007

(65) Prior Publication Data

US 2007/0209089 A1 Sep. 6, 2007

Related U.S. Application Data

(60) Provisional application No. 60/765,177, filed on Feb. 6, 2006.

(51) Int. Cl.
*C12N 15/84* (2006.01)
*C12N 15/54* (2006.01)
*A01H 4/00* (2006.01)

(52) U.S. Cl. ........ 800/290; 800/282; 800/284; 800/294; 800/317.2; 435/193; 435/429; 435/430; 435/431; 435/469

(58) Field of Classification Search .................. None
See application file for complete search history.

(56) References Cited

U.S. PATENT DOCUMENTS

| | | |
|---|---|---|
| 6,326,192 B1 | 12/2001 | Sugita et al. |
| 6,407,312 B1 | 6/2002 | Banno et al. |
| 6,441,276 B1 | 8/2002 | Ikeda et al. |
| 6,452,068 B1 | 9/2002 | Zuo et al. |
| 6,521,458 B1 | 2/2003 | Gutterson et al. |
| 7,250,554 B2 * | 7/2007 | Rommens et al. ............ 800/278 |
| 2003/0221213 A1 | 11/2003 | Rommens et al. |
| 2004/0107455 A1 | 6/2004 | Rommens et al. |
| 2004/0237142 A1 | 11/2004 | Gilbertson et al. |

FOREIGN PATENT DOCUMENTS

| | | |
|---|---|---|
| WO | WO 03/069980 A2 | 8/2003 |
| WO | WO 03/079765 A2 | 10/2003 |
| WO | WO 2004/092390 A2 | 10/2004 |
| WO | WO 2005/004585 A2 | 1/2005 |

OTHER PUBLICATIONS

Inze et al. Molecular and General Genetics 194: 265-274 (1984).*
Thomashow et al. Science 231: 616-618 (Feb. 1986).*
Richael et al. Transgenic Research 17: 905-917 (2008).*
Aronen, Tuija S. et al., "Applicability of the Co-Inoculation Technique Using *Agrobacterium tumefaciens* Shooty-Tumour Strain 82.139 in Silver Birch," *Plant Cell*, vol. 70, pp. 147-154 (2002).
Dale et al., "Gene Transfer with Subsequent Removal of the Selection Gene from the Host Genome," *Proc. Natl. Acad. Sci. USA*, vol. 88, pp. 10558-10562 (1991).
Dale et al., "Potential for the Environmental Impact of Transgenic Crops," *Nat. Biotech.* vol. 20, pp. 567-574 (2002).
Ebmeier et al., "Evaluation of the *Escherichia coli* Threonine Deaminase Gene as a Selectable marker for Plant Transformation," *Plants*, vol. 218, pp. 751-758 (2004).

Fraley et al., "Expression of Bacterial Genes in Plant Cells," *Proc. Natl. Acad. Sci. USA*, vol. 80, pp. 4803-4807 (1983).
Heeres, et al., "Transformation of a Large Number of Potato Varieties: Genotype-Dependent Variation in Efficiency and Somaclonal Variability," *Euphytica*, vol. 124, pp. 13-22 (2002).
Huang et al., "Generation of Marker-Free Transgenic Maize by Regular Two-Border *Agrobacterium* Transformation Vectors," vol. 13, pp. 451-461 (2004).
Joersbo et al., "Parameters Interacting with Mannose Selection Employed for the Production of Transgenic Sugar Beet," *Physiologia Plantarum*, vol. 105, pp. 109-115 (1999).
Kakimoto, Tatsuo, "CKI1, a Histidine Kinase Homolog Implicated in Cytokinin Signal Transduction," *Science*, vol. 274, pp. 982-985 (1996).
Kilby et al., "FLP Recombinase in Transgenic Plants: constitutive Activity in Stable Transformed Tobacco and Generation of Marked Cell Clones in *Arabidopsis*," *The Plant Journal*, vol. 5, pp. 637-652 (1995).
Kononov et al., "Integration of T-DNA Binary. Vector 'backbone' Sequences Into the Tobacco Genome: Evidence for Multiple Complex Patterns of Integration," *The Plant Journal*, vol. 11, No. 5, pp. 945-957 (1997).
Li et al., "Altered Morphology in Transgenic Tobacco Plants that Overproduce Cytokinins in Specific Tissues and Organs," *Developmental Biology*, vol. 153, pp. 386-395 (1992).
Luo et al., "The Maize Knotted1 Gene is an Effective Positive Selectable Marker Gene for *Agrobacterium*-Mediated Tobacco Transformation," *Plant Cell Rep.* vol. 25, pp. 403-409 (2006).
MacHackova et al., "Growth Pattern, Tuber Formation and Hormonal Balance in in vitro Potato Plants Carrying *ipt* Gene," *Plant Growth Regulation*, vol. 21, pp. 27-36 (1997).
Mihalka et al., "Binary Transformation Systems Based on 'Shooter' Mutants of *Agrobacterium tumefaciens*: a Simple, Efficient and Universal Gene Transfer Technology that Permits marker Gene Elimination," vol. 21, pp. 778-784 (2003).
Puchta, Holger, "Marker-Free Transgenic Plants," *Plant Cell Tiss. Organ Cult.*, vol. 74, pp. 123-134 (2003).
Rommens, C.M., "Crop Improvement through Modification of the Plant's Owned Genome," *Plant Physiology*, May 2004, vol. 135, pp. 421-431.
Smyth, et al., "Liabilities and Economics of Transgenic Crops," *Nat. Biotech.*, vol. 20, pp. 537-541, (2002). Srinivasan, et al., "Heterologous Expression of the *BABY BOOM AP2/ERF* Transcription Factor Enhances the Regeneration Capacity of Tobacco (*Nicotiana tabacum L.*)," *Plants*, vol. 225, pp. 341-351, (2007).
Sugita et al., "A Transformation Vector for the Production of Marker-free Transgenic Plants Containing a Single Copy Transgene at High Frequency", *Plant Journal*, Jun. 2000, vol. 22, No. 5, pp. 461-469.
Waldron, et al., "Resistance to Hygromycin B," *Plant Mol. Biol.* vol. 5, pp. 103-108 (1985).
Weeks, et al., "Wheat Transformation Using Cyanamide as a New Selective Agent," *Crop Sci.*, vol. 40, pp. 1749-1754 (2000).
Zubko et al., "Modification of Cytokinin Levels in Potato via Expression of the *Petunia hybrida Sho* Gene," *Transgenic Res.*, vol. 14, pp. 615-618 (2005).

(Continued)

Primary Examiner — David T Fox
(74) Attorney, Agent, or Firm — Foley & Lardner LLP

(57) ABSTRACT

The present invention provides a convenient method for producing a transformed plant by expressing a hormone gene positioned within a plasmid backbone that also carries a P-DNA or T-DNA to obtain backbone-free transformed plants.

21 Claims, 3 Drawing Sheets

OTHER PUBLICATIONS

Ebinuma et al., "Systems for Removal of a Selection Marker and their Combination with a Positive Marker", *Plant Cell Rep.*, 2001, vol. 20, pp. 383-392.

Richael et al., 2006 In Vitro Biology Meeting, 2006 Meeting of the Society for In Vitro Biology Jun. 3-7, "Employment of Efficient Marker-free Transformation Methods" by Late Submission Abstracts, [Online] Jun. 2006 URL:http//www.sivb.org/2006LateAbstracts.pdf Minneapolis, MN.

Vetten et al., "A Transformation Method for Obtaining Marker-Free Plants of a Cross-Pollinating and Vegetatively Propagated Crop", Apr. 2003, pp. 439-442, vol. 21, *Nature Biotechnology*.

\* cited by examiner

FIGURE 1. Normal (*ipt* negative) versus abnormal (*ipt*-positive) phenotype in tobacco and potato. Plants overexpressing *ipt* tend to lack apical dominance resulting in a shooty, highly branched habit. They also tend to be chlorotic and root poorly or not at all on MS medium without hormones. Ipt positive shoots are illustrated on the right of each picture.
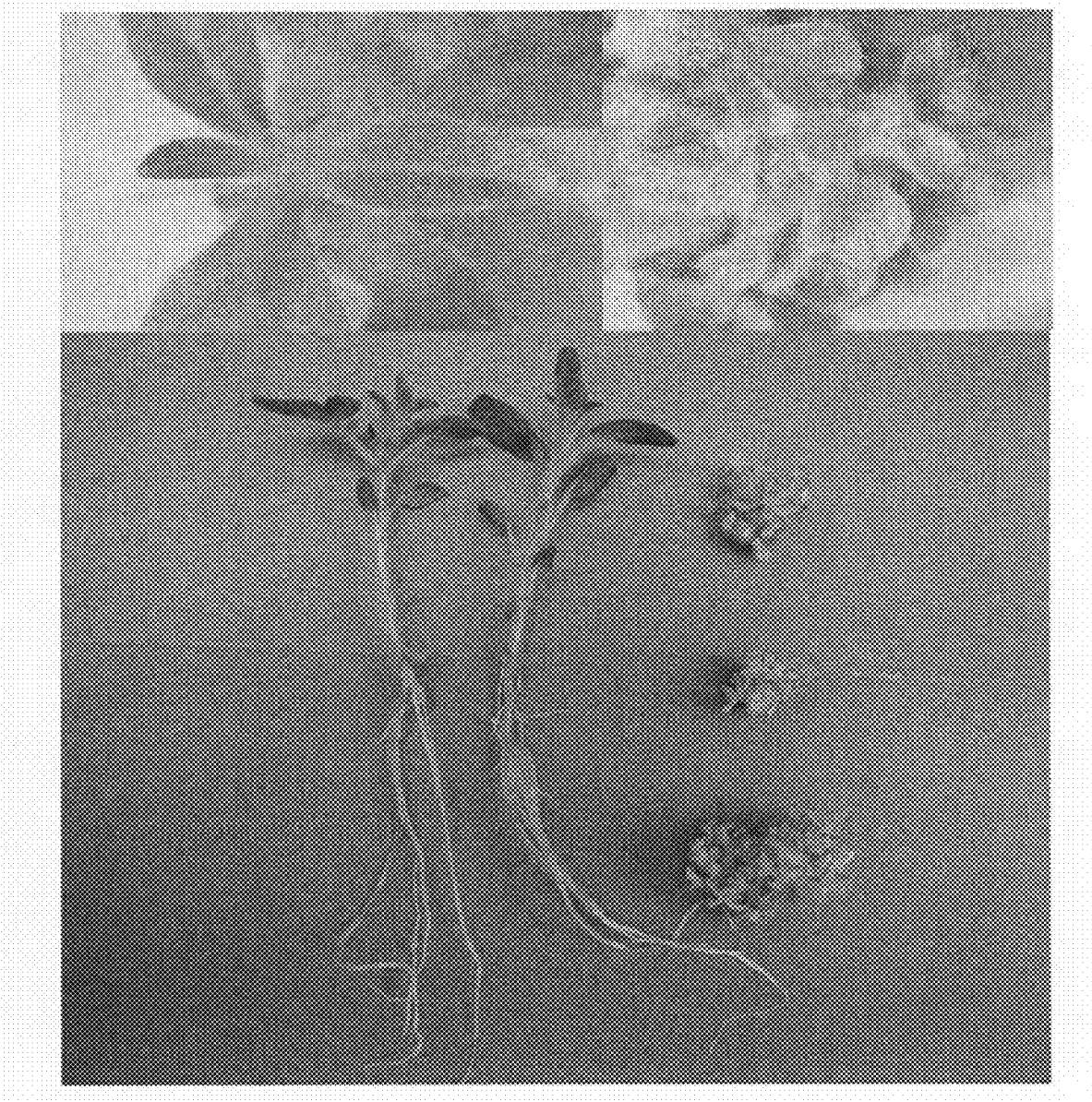

Figure 2. Schematic showing the basis structure of the binary plasmid described in this invention. The transfer DNA (P-DNA or T-DNA) is delineated by the right (RB) and left (LB) border and contains the gene of interest (GOI). The region outside the transfer DNA is refer to as the backbone and contains the plant hormone biosythetic gene (ipt).
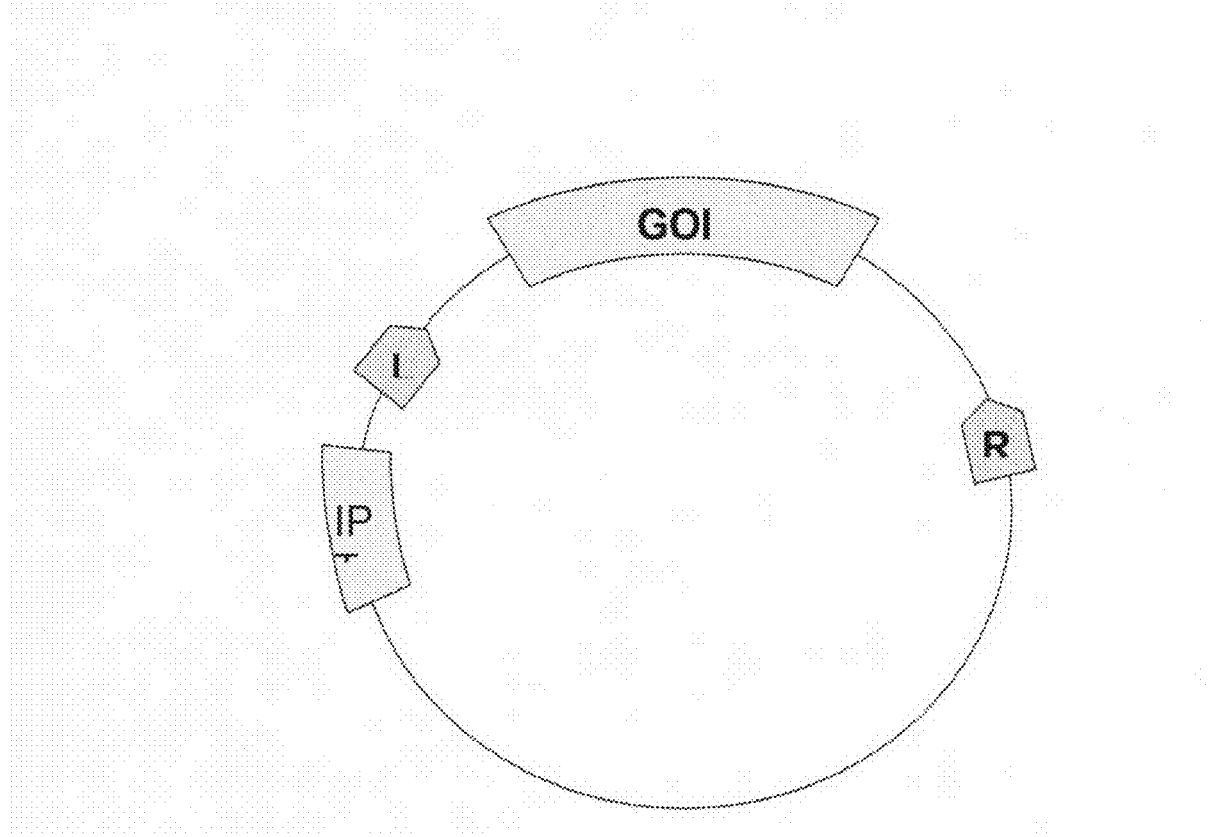

Figure 3. Structure of complex P-DNA
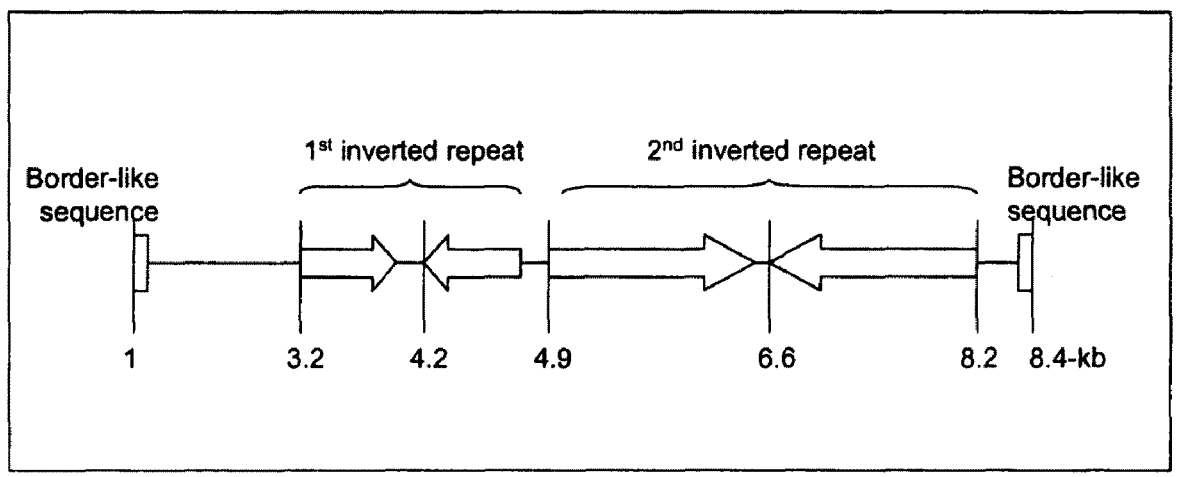

GENERATION OF MARKER-FREE AND BACKBONE-FREE TRANSGENIC PLANTS USING A SINGLE BINARY APPROACH

This U.S. Non-Provisional Application claims priority to U.S. Provisional Application Ser. No. 60/765,177 filed on Feb. 6, 2006, which is incorporated herein by reference.

FIELD OF THE INVENTION

The present invention provides a convenient method for producing a transformed plant. This method requires expression of a hormone gene positioned within a plasmid backbone that also carries a P-DNA or T-DNA to obtain backbone-free transformed plants.

BACKGROUND

As is well appreciated, *Agrobacterium tumefaciens* is a useful bacteria for delivering and integrating desired nucleic acids, such as desirable transgenes, into a plant cell genome. The bacterium's transfer DNA (T-DNA) is the vehicle that shuttles the transgene from the tumor-inducing plasmid contained within the bacterium strain and into the plant's genetic material. The agricultural industry exploits this capability in order to genetically modify crops to express desirable genes and traits.

Typically, a selectable marker gene is positioned alongside the transgene in the T-DNA, so that it is integrated into the plant genome along with the transgene. The expression of the marker helps to identify those cells that contain an integrated transgene. Some common markers include bacterial antibiotic resistance genes, such as neomycin phosphotransferase, "nptII" (Fraley et al., Proc. Natl. Acad. Sci. 80:4803-4807, 1983) and hygromycin phosphotransferase, "hpt" (Waldron et al., Plant Mol. Biol. 5:103-108, 1985). Other bacterial fungal markers include the fungal mycotoxin resistance gene, cyanamide hydratase, "cah" (Weeks et al., Crop Sci. 40:1749-1754, 2000), phosphomannose isomerase, "manA" or "pmi" (Joersbo et al., Physiol. Plant 105:109-115, 1999) and threonine deaminase, "TD" (Ebmeier et al., Planta 218:751-758, 2004).

It is possible to co-assign a marker to a specific gene and thereby devise a T-DNA, which contains multiple genes and multiple markers for ultimate integration into a plant genome. Thus, this so-called "gene stacking" strategy combines several desired traits into one plant line. The ability to stack numerous genes, however, depends on the availability and appropriateness of the co-assigned markers. Hence, gene stacking can be limited by its dependence on marker genes.

Another concern, is that some believe markers pose potential risks to human and animal health and to the environment. For instance, there is concern that antibiotic- and herbicide-resistance genes may escape from the plants into which they are engineered and into the environment. Thus, those resistance genes, outside of the modified plant's genome, may confer an adaptive advantage to weeds and pathogens that take them into their own genomes (Dale et al., Nat. Biotech. 20:567-574, 2002).

Accordingly, several strategies have been devised to excise a selectable marker from a transgenic plant. One such method employs site-specific recombinase enzymes to remove the marker from its locus in the plant genome. See Dale and Ow, Proc. Natl. Acad. Sci. 23:10558-10562, 1991; Kilby et al., Plant J. 8:637-652, 1994; and Sugita et al., Plant J. 22:461-469, 1999. The removal success rate, however, is quite low. Furthermore, the excision process typically leaves foreign DNA elements embedded in the plant genome.

Another method involves elimination of markers from the plant genome by co-transformation. This strategy essentially entails delivering and integrating the gene of interest and its marker into the plant genome using two T-DNAs. The idea is that it is easier to cross-out the marker from the plant line, while retaining the desired gene, because the gene and marker are not linked genetically. Hence, two distinct integration events must occur thereby permitting the distinct marker T-DNA element to be backcrossed out or otherwise segregated from the distinct gene because they exist at unlinked locations.

The T-DNAs that contain the marker and the gene may exist within the same binary vector or on different binaries. Similarly, a T-DNA containing a marker may be on a plasmid that is contained within an *Agrobacterium* strain that is the same or different as the strain containing the plasmid with the desired gene or in the backbone of a single binary vector. See Puchta, Plant Cell Tiss. Organ Cult., 74:123-134, 2003, and Huang et al., Transgen. Res. 13:451-461, 2004.

Unfortunately, these marker-removal strategies are time-consuming and can be financially draining, which is problematic because it is the absence of marker genes that helps to lower the cost of de-regulation and facilitate commercialization of genetically modified crops (Smyth et al., Nat. Biotech 20:537-541, 2002). More importantly, these strategies are useless in crops that are sterile and they cannot be applied to clonally-propagated crops such as potato.

Yet an added concern is not only the removal of the marker gene but the fact that *Agrobacterium*-mediated transformation more often than not introduces unnecessary plasmid backbone DNA sequences into the plant genome. That is, the enzymes that splice the T-DNA from the plasmid vector do not always cut the plasmid precisely. For example, the enzymes may cut the plasmid beyond the ends of the T-DNA, which are delineated by left and right border sequences that serve as recognition cleavage sites for those enzymes. Hence, the T-DNA, once spliced from the plasmid, may be longer than expected and thereby carry plasmid backbone sequences in addition to the marker and gene of interest.

These backbone sequences also can integrate into the plant genome. Indeed, 75% of all integration events contain backbone elements in *Solanaceous* species (Kononov et al., Plant J. 11:945-957, 1997; Heeres et al., Euphytica 124:13-22, 2002; Rommens et al., Plant Physiol. 135:421-431, 2004).

This is an added concern because the backbone sequences of tumor-inducing plasmids that are used in *Agrobacterium*-mediated transformation contain many different genetic elements, such as origins of replication, bacterial selectable marker genes, and other foreign regulatory elements. Agricultural and environmental authorities often find the presence of such extraneous foreign DNA in a plant genome to be unacceptable, despite the benefits conferred by expression of the co-integrated gene of interest.

Accordingly, in addition to devising strategies for removing markers, strategies also must be developed to identify those transgenic plants that also contain plasmid backbone sequences. These include polymerase chain reaction-based amplification and Southern blotting to identify the retention of known plasmid sequences in the plant's genetic makeup. Both screening methods are tedious and expensive, especially when backbone integration frequencies are high.

Placing lethal genes in the backbone to eliminate cells that are transformed with the backbone is potentially useful. See U.S. Pat. No. 6,521,458. Such genes, however, can cause problems to surrounding cells, such as impairing their ability to regenerate.

The conditionally-lethal gene cytosine deaminase, (codA), converts non-toxic 5-fluorocytosine (5-FU) to toxic 5-fluorouracil. 5-FU is known to migrate, however, to cells that do not contain any plasmid backbone sequences. Moreover, the method of using conditionally-lethal genes require the addition of exogenous substrates, which means another step in medium preparation or explant transfer.

The use of non-lethal marker genes in the backbone has been suggested as an alternative to lethal, conditionally lethal or scorable genes, such as GUS, beta glucuronidase. See U.S. patent application publication U.S. 2004/0237142.

The non-lethal genes provide a visual means to distinguish transgenic events that contain the vector backbone. Such genes include any that are involved in plant hormone biosynthesis, plant hormone degradation, plant hormone signaling, or metabolic interference.

This method identifies the transgenic plants that contain plasmid DNA without doing PCR or Southern blot screening, but it requires the use of a positive selection marker within the T-DNA and, therefore, is not a marker-free method.

One method was developed that exploited the utility of the marker gene, while selecting against its integration. By employing positive selection for transient marker gene expression followed by negative selection against marker gene stable integration, roughly 25% of regenerated plants contain the transgene of interest but no marker gene. See Rommens et al., Plant Physiol. 135:421-431, 2004, which is incorporated herein by reference.

Another method employs "armed" *Agrobacterium* strains that still contain their own hormone genes (Mihalka et al., Plant Cell Rep. 21:778-784, 2003, Aronen et al. Plant Cell Tissue Organ Cult. 70:147-154, 2002). A gene of interest is engineered into a disarmed binary plasmid and introduced into special "shooter" mutants that contain a native, oncogenic (or "armed") Ti plasmid. Although this method will generally provide marker-free shoots at low frequency, it requires the use of special oncogenic strains. Another problem is the probability of having an backbone integration event with the gene of interest is compounded by the use of two binaries rather than one.

The present invention details a new method that requires expression of a hormone synthesis gene or genes positioned within the backbone of a plasmid having a transfer DNA (P-DNA or T-DNA). The hormone synthesis gene drives regeneration of marker-free plants harboring the transfer DNA. Selection against integration of backbone sequences is accomplished at regeneration and therefore, simplifies the identification of events without superfluous DNA sequences.

SUMMARY

In one aspect, the present invention provides a method for producing a transgenic plant that does not contain a selectable marker in its genome, comprising (a) transforming a plant cell with a plasmid that comprises (i) a transfer-DNA that does not contain a gene for a selectable marker and (ii) a cassette, positioned outside of the transfer-DNA, for expressing a hormone gene or genes; (b) culturing the transformed cells on hormone-poor medium to produce shoots; (c) identifying a shoot that has genomic DNA containing the transfer-DNA but not the hormone gene expression cassette; and (d) growing a plant from the identified shoot of (c), wherein the plant is a transgenic plant that does not contain a selectable marker in its genome.

In a preferred embodiment, the hormone gene is an isopentenyl transferase gene.

In another embodiment, the expression of a nucleic acid sequence in the transfer-DNA modifies a trait in the resultant transgenic plant, wherein the trait is at least one of (i) lower levels of acrylamide, (ii) reduced black-spot bruising, and (iii) reduced cold-induced sweetening in comparison to a plant that does not comprise a cell that expresses that nucleic acid sequence.

In a preferred embodiment, the transgenic plant has a lower level of acrylamide in comparison to a plant that does not comprise a cell that expresses the nucleic acid sequence in the transfer-DNA.

In another embodiment, the plasmid is in an *Agrobacterium* strain and the transforming step comprises contacting the plant cell with the *Agrobacterium* strain.

In one embodiment, the transfer-DNA comprises nucleic acid sequences that are native to the genome of the plant cell.

In another aspect, the present invention provides a method for producing a transgenic plant that does not contain a selectable marker in its genome, comprising (a) transforming a plant cell with a plasmid that comprises (i) a transfer-DNA that does not contain a gene for a selectable marker and (ii) a cassette, positioned outside of the transfer-DNA, for expressing a hormone gene; (b) culturing the transformed cells on hormone-poor medium to produce shoots; (c) growing the shoots into plants; and (d) identifying a plant that has genomic DNA that contains the transfer-DNA but not the hormone gene expression cassette, wherein the plant of (d) is a transgenic plant that does not contain a selectable marker in its genome.

According to the present invention, transformed plant cells may be cultured on a medium categorized as hormone-poor or hormone-restricted, which are interchangeable terms. Such a medium, in contrast to hormone-free media, which has zero levels of hormones such as cytokinins and auxins, the hormone-poor medium comprises some amount of such hormones. One characteristic of the hormone-poor medium, however, is that it contains a concentration of hormone at a level that (i) does not promote the regeneration untransformed shoots but (ii) does improve regeneration of shoots produced through cytokinin gene expression.

In one embodiment, the hormone-poor medium comprises at least one of an auxin, cytokinin, and thidiazuron. In one embodiment, the auxin is 1-naphthaleneacetic acid (NAA) or indole-3-acetic acid (IAA). In one embodiment, the cytokinin is zeatin riboside or 6-benzylaminopurine (BAP). In another embodiment, the concentration of an auxin in the hormone-poor medium is about 0.05 mg/l, about 0.06 mg/l, about 0.07 mg/l, about 0.08 mg/l, about 0.09 mg/l, about 0.10 mg/l, about 0.11 mg/l, about 0.12 mg/l, about 0.13 mg/l, about 0.14 mg/l, about 0.15 mg/l, about 0.16 mg/l, about 0.17 mg/l, about 0.18 mg/l, about 0.19 mg/l, about 0.20 mg/l, about 0.21 mg/l, about 0.22 mg/l, about 0.23 mg/l, about 0.24 mg/l, about 0.25 mg/l, about 0.26 mg/l, about 0.27 mg/l, about 0.28 mg/l, about 0.29 mg/l, about 0.30 mg/l, about 0.31 mg/l, about 0.32 mg/l, about 0.33 mg/l, about 0.34 mg/l, about 0.35 mg/l, about 0.36 mg/l, about 0.37 mg/l, about 0.38 mg/l, about 0.39 mg/l, or about 0.40 mg/l.

In another embodiment, the concentration of the cytokinin in the hormone-poor medium is about 0.05 g/l, about 0.06 g/l, about 0.07 g/l, about 0.08 g/l, about 0.09 g/l, about 0.10 g/l, about 0.11 g/l, about 0.12 g/l, about 0.13 g/l, about 0.14 g/l, about 0.15 g/l, about 0.16 g/l, about 0.17 g/l, about 0.18 g/l, about 0.19 g/l, about 0.20 g/l, about 0.21 g/l, about 0.22 g/l, about 0.23 g/l, about 0.24 g/l, about 0.25 g/l, about 0.26 g/l, about 0.27 g/l, about 0.28 g/l, about 0.29 g/l, or about 0.30 g/l.

In another embodiment, the concentration of thidiazuron in the hormone-poor medium is about 0.01 μM, about 0.02 μM, about 0.03 μM, about 0.04 μM, about 0.05 μM, about 0.06 μM, about 0.07 μM, about 0.08 μM, about 0.09 μM, about 0.10 μM, about 0.11 μM, about 0.12 μM, about 0.13 μM, about 0.14 μM, about 0.15 μM, about 0.16 μM, about 0.17 μM, about 0.18 μM, about 0.19 μM, about 0.20 μM, about 0.21 μM, about 0.22 μM, about 0.23 μM, about 0.24 μM, about 0.25 μM, about 0.26 μM, about 0.27 μM, about 0.28 μM, about 0.29 μM, about 0.30 μM, about 0.4 μM, about 0.5 μM, about 0.6 μM, about 0.7 μM, about 0.8 μM, about 0.9 μM, about 1 μM, about 2 μM, or about 3 μM.

In another embodiment, the plant cells are from a dicotyledonous plant selected from the group consisting of potato, tobacco, tomato, sugarbeet, broccoli, cassaya, canola, sweet potato, pepper, cotton, poinsettia, legumes, alfalfa, soybean, carrot, strawberry, lettuce, oak, maple, walnut, rose, mint, squash, daisy, apple, pear, cherry, plum, and cactus.

In one embodiment, the plant cells are potato plant cells. In one embodiment, the potato plant cells are from a cultivar, such as Russet Ranger or Bintje. In one embodiment, the potato variety is Russet Atlantic, All Blue, Purple Valley, and Borah Valley In one other embodiment, the plant cells are from a monocotyledenous plant selected from the group consisting of wheat, turf, turf grass, cereal, maize, rice, oat, wheat, barley, sorghum, orchid, iris, lily, onion, banana, sugarcane, sorghum, and palm.

BRIEF DESCRIPTION OF THE FIGURES

FIG. 1: normal (ipt negative) versus abnormal (ipt-positive) phenotype in tobacco and potato. Plants overexpressing ipt tend to lack apical dominance resulting in a shooty, highly branched habit. They also tend to be chlorotic and root poorly or not at all on MS medium without hormones. Ipt positive shoots are illustrated on the right of each picture.

FIG. 2. Schematic diagram illustrating one binary plasmid embodiment of the present invention. The transfer DNA, which can be a P-DNA or a T-DNA, is delineated by the right (RB) and left (LB) border and contains the gene of interest (GOI). The region outside the transfer DNA is refer to as the backbone and contains the plant hormone biosythetic gene (ipt).

FIG. 3: Schematic representation of one exemplary embodiment for a P-DNA.

DETAILED DESCRIPTION

The present inventive method uses an *Agrobacterium* binary plasmid that contains a plant-derived transfer-DNA (P-DNA) instead of an *Agrobacterium* T-DNA. The P-DNA is delineated by DNA sequences that come from the plant genome and facilitate enzymatic nicking of the plasmid in *Agrobacterium*. Hence, the P-DNA is also able to serve as a vehicle for shuttling desired genes and polynucleotides of interest into a plant genome, but it is not foreign to the plant genome.

Thus, the binary plasmid of the present invention contains a gene of interest inserted within the borders of the P-DNA, and a plant hormone biosynthetic gene in the plasmid's backbone, outside of the P-DNA (patent applications 2003/0221213A1 and US2004/0107455A1). Alternatively, the plasmid can contain one P-DNA border and an oriT sequence as replacement for the second border. It is also possible to use T-DNA borders or combinations of P-DNA borders and T-DNA borders (provisional patent application 058951-0241). Expression of the plant hormone biosynthetic gene drives regeneration of normal marker-free shoots and serves as a visual marker of backbone integration within the plant genome. The plasmid of the present invention is transformed into a suitable *Agrobacterium* cell that will deliver the above construction into plant cells.

A plasmid "backbone" is any portion of the DNA sequence of binary vector outside the transfer DNA region. Backbone comprises any non-transfer DNA of the binary including the bacterial replicon region of the vector and antibiotic resistance sequences for vector maintenance.

Plant hormone biosynthetic genes include any sequence shown to directly or indirectly promote the synthesis of cytokinins, auxins, gibberellin, or brassinosteroids that drive the division, elongation and the differentiation of plant cells into shoots, roots or embryos. Such sequences include the isopentenyl transferase gene (ipt), cytokinin-independent 1 (CDK-1) gene, the ESR-2 and ESR-1A genes, the Sho gene, the Knl gene, the iaaH/M genes, and the BBM gene.

Conventional plant regeneration methods require media that contain high hormone concentrations. Typically, auxins are used for cell proliferation and callus formation, cytokinins for cell development and shoot regeneration, and gibberellic acid for cell expansion. As hormone levels are reduced, transformation frequencies reduce and will become too low to generate plants. The current invention is based on the use of binary vectors that contain an expression cassette for a hormone gene or genes in the vector backbone. Expression of such a genes results in the production of, for instance, cytokinin or auxin. Consequently, the media used to produce transformed shoots according to the current invention contain low hormone concentrations. Preferably, the media contain less than about 10% of the hormone concentrations that are present in conventional media. Most preferably, these new media do not contain any hormones.

The invention thus provides a method for creating marker-free, backbone-free transgenic crop plants. It provides a means for the selection of commercially acceptable plants without foreign DNA elements such as antibiotic resistance genes and bacterial genetic elements. With the use of plant-derived border (P-DNAs) and transgenes from plant sources, it becomes practical to create all native transgenics using this method.

The present invention uses a DNA plasmid that contains a plant hormone biosynthetic gene cassette located in a region outside of a P-DNA and associated with plasmid maintenance DNA otherwise known as vector backbone DNA. The isopentenyl transferase (ipt) gene, when stably expressed in a transgenic plant cell, induces the regeneration of physiologically and morphologically aberrant plants (see FIG. 1). Plant arising from cells stably transformed with ipt show an abnormal morphology because of the constant production of cytokinin (Li et al., Devel. Biol., 153:386-395, 1993; Machackova et al., Plant Growth Reg. 21:27-36, 1997). The ipt gene was isolated from *Agrobacterium tumefaciens* and encodes the enzyme producing the first intermediate in cytokinin biosynthesis. Consequently, ipt used in the backbone becomes a visual marker of backbone integration events. Others utilize the ipt gene in such a way to eliminate plants containing undesirable backbone sequences (US Patent Application US2004/0237142A1 and Rommens et al. 2004, which are incorporated herein by reference).

In the present invention, the tendency of ipt overexpression to induce the regeneration of plants with normal phenotypes that display apical dominance and root readily on hormone-free medium is exploited. A percentage of these normal shoots have the transgene of interest engineered within the P-DNA. This method is generally more efficient at producing marker-free shoots than previously published methods (Mihalka et al., Plant Cell Rep. 21:778-784, 2003) and has the added benefit of selecting against backbone integration. No special "shooter" mutants are needed and binary construction is straightforward, requiring only the addition of an plant hormone biosynthetic gene expression cassette in the backbone.

Methods using inducible promoters linked to the ipt gene placed within the T-DNA borders have been described. (U.S. Pat. Nos. 6,452,068 and 6,326,192). This strategy employs ipt to drive regeneration and circumvents the problem of aberrant morphology created by constant expression of ipt. However, transgenic plants will continue to carry the ipt gene. The present invention uses ipt to drive regeneration but eliminates the need of creating such a complex vector and allows the generation of marker-free, foreign DNA-free transgenics. The present invention obviates the induction step as well. In the present invention, the ipt gene is preferably constitutively expressed.

Plant hormone biosynthetic genes include the cytokinin-independent 1 (CDK-1) gene that also provides an ipt-like phenotype (Kakimoto, Science 274:982-985, 1996). Other cytokinin biosynthetic genes include, but are not limited to, ESR-2 (U.S. Pat. No. 6,441,276) and ESR-1A (U.S. Pat. No. 6,407,312), the Sho gene (Zubko et al., Transgenic Res. 14:615-618), the Knl gene (Luo et al., Plant Cell Rep. 25:403-409) and the BBM gene (Srinivasan et al. 2007, Planta 225: 341-351).

The vector used to demonstrate this system is previously described in Rommens et al. 2004 (US patent application 2003/0221213A1, which is incorporated herein by reference). Instead of being a typical T-DNA vector, the T-DNA borders are replaced with plant border-like sequences. This plant DNA (P-DNA) supports an effective transfer of DNA from *Agrobacterium* binary plasmids to the genome of plant cells. The generation of intragenic plants with no foreign DNA is facilitated by the derivation of such P-DNAs.

EXAMPLES

Example 1

DNA Vectors for Proof-of-concept Experiments

Here is demonstrated the use of a single binary with a plant hormone biosynthetic gene like the isopentenyl transferase cytokinin gene (ipt) in the backbone and the gene of interest in the P-DNA to generate marker-free, backbone-free plants. The genetic constructs contain the gene of interest nptII, (neomycin phosphotransferase II) within P-DNA left and right borders driven by a constitutive promoter expressed in the callus and developing plantlet (e.g. Ubiquitin-7 promoter) terminated by the 3'-termination sequence of the ubiquitin-3 gene. Within the backbone of the same binary is inserted the hormone gene(s) driven by the ubiquitin promoter and terminated by the 3'-termination sequence of the ubiquitin-3 gene. The hormone gene cassette is placed close to the left border sequence (240 base pairs of backbone sequence separate the ubiquitin-3 terminator from the start of the left border). Placing the hormone synthetic gene cassette as close to the left border as possible maximizes the utility of gene(s) as a marker against backbone integration as the *Agrobacterium* endonuclease VirD2 can cut within the backbone at random sites rather than at the LB. The basic design of a plasmid of the present invention is illustrated in FIG. 2. The control vector contains an identical P-DNA expression cassette but does not contain the plant hormone biosynthetic gene(s) in the vector backbone. The gene of interest can be any number of scorable, screenable or agronomic genes but nptII was chosen as a easily screenable marker for the purpose of experimentation. The right and left border elements may be substituted with other like elements that function as nick sites for *Agrobacterium* endonucleases but one would expect deviations from the results demonstrated in the present invention.

Example 2

Production of Transformed and Backbone-free Potato Plants Containing Test Constructs Disarmed *Agrobacterium tumefaciens* strains (such as LBA4404) are used to deliver the P-DNA containing the gene of interest NptII and backbone containing the ipt gene into the cells of the internodal explants of potato. Ten fold dilutions of overnight cultures of the *Agrobacterium* harboring this vector were grown for 5 to 6 hours. This culture was precipitated at 2800 rpm, washed with MS liquid medium (1×MS salts, 3% sucrose, pH 5.7) and resuspended in the same to make a 0.2 $OD_{600}$. Co-cultivation of *Agrobacterium* with potato explants occurred on co-culture medium (0.1×MS salts, 3% sucrose, 0.7% phytagar, pH 5.7) for 2 days. After co-cultivation, explants are transferred to hormone-free Murashige/Skoog medium (1×MS salts, 3% sucrose, 0.7% phytagar, pH 5.7) and 150 mg/ml timentin to eliminate *Agrobacterium*. Alternatively, explants could be transferred to media containing auxin (eg. NAA at 0.1 mg/l) or cytokinin (e.g. zeatin riboside at 0.25 g/l) at levels that do not promote the regeneration untransformed shoots but improve regeneration of shoots produced through ipt expression.

After one month explants were transferred to new medium of the same make-up. Depending on the cultivar and growing conditions, shoots appear after about a months time. This is not true for explants infected with the control vector. No shoots arise from such control explants. During the second month, one normal looking shoot is excised from each explant that provides one. Generally, not more that one shoot is taken so that clones of a single transformation event are not confounding the final results. Shoots with normal phenotypes are observed to root on MS medium without hormones and do not have a branching, multiple shoot and chlorotic appearance. A tissue sample is taken for PCR analysis to verify the presence of the gene of interest and the absence of backbone sequences.

Potato internodal explants typically produced shoots within 4 to 6 weeks on hormone-free MS medium. The cultivar Bintje produced more shoots per explants and initiated shoot formation sooner than cultivar Russet Ranger. In two independent experiments, 75% and 89% of all explants of cv. Bintje produced at least one normal shoot (non-shooty, displaying apical dominance). This differs slightly from cv. Ranger where only 59% of explants formed at least one normal shoot.

Application of the method to other varieties such as Atlantic, All Blue, Purple Valley, and Borah Valley was also found to yield shoots within about 4-6 weeks after explant infection.

A polymerase chain reaction (PCR) based method is used to score plants for the presence or absence of P-DNA (nptII cassette) and vector backbone (ipt cassette) sequences. The ipt cassette is adjacent to the LB and a PCR positive result for it indicates that transfer of the vector sequences beyond the LB has occurred. Table 1 shows the results of PCR analysis.

In experiments using cv. Bintje, both phenotypic and molecular analyses demonstrated that an average of 5% of normal-looking backbone-free (having apical dominance, not shooty) shoots are positive for the gene of interest. In experiments using cv. Ranger, PCR for the gene of interest indicated that an average of 7% of normal-looking (having apical dominance, not shooty) shoots are positive for the gene of interest.

When cv. Bintje was transformed using a binary utilizing T-DNA borders instead of P-DNA borders, it was determined that frequencies of backbone-free and marker free plants is comparable to that obtained with P-DNA borders (Table 1).

These results show the benefit conferred by adding a constitutively expressed ipt cassette to the backbone to eliminate backbone integration events. Also apparent is the simplicity of using this strategy where no hormones are needed to regenerate marker-free shoots and no amendments are added to the media to eliminate backbone sequences.

Example 3

Production of Transformed and Backbone-free Tomato Plants Containing Test Constructs Sterilized tomato seeds (cv. MoneyMaker) are germinated on MS medium solidified with gelrite (1%) at 24 C with a 16-h photoperiod. Seedlings are grown for 8 days before explanting at which time each cotyledon is cut into 3 pieces in a under liquid MS medium and hypocotyls are cut into 10 mm long segments.

Disarmed *Agrobacterium tumefaciens* strains (such as LBA4404) are used to deliver the P-DNA containing the gene of interest NptII and backbone containing the ipt gene into the cells of the explants of tomato. After co-cultivation, explants are transferred to hormone-free Murashige/Skoog medium (1×MS salts, 3% sucrose, 0.7% phytagar, pH 5.7) and 150 mg/ml timentin to eliminate *Agrobacterium*. Alternatively, explants can be transferred to media containing auxin (e.g. IAA at 0.1 mg/l) or cytokinin (e.g. zeatin riboside at 0.2 g/l) at levels that do not promote the regeneration of untransformed shoots. Tomato hypocotyl explants of cultivar MoneyMaker produce shoots in 4-8 weeks on hormone-free or hormone limited MS medium. Tomato cotyledon explants did not form shoots on hormone-free MS medium demonstrating the need to find the proper explant material for the method described in the invention. Only one shoot with a normal appearance was excised from each explant to ensure that replicates of a single transformation event were not taken. Once shoots had rooted, a leaf tissue sample was taken for PCR analysis. Only rooted, normal appearing shoots were sampled for later molecular verification. Plants containing the ipt cassette were distinctly abnormal with multiple shoots, a chlorotic color and inability to root effectively on hormone-free MS medium.

Table 2 shows the results of phenotypic and PCR analysis. Two independent trials with tomato (cv. MoneyMaker) demonstrated that 2% of normal-looking (having apical dominance, not shooty) were positive for the transgene of interest and negative for backbone.

Example 4

Production of Transformed and Backbone-free Tobacco Plants Containing Test Constructs Leaf pieces from 4- to 6-week-old in vitro aseptic *Nicotiana tabacum* cv. Petite Havana plants, cut into squares of about 0.5 cm² are used as explants. Disarmed *Agrobacterium tumefaciens* strains (such as LBA4404) are used to deliver the P-DNA containing the gene of interest NptII and backbone containing the ipt gene into the cells of the leaf explants of tobacco. After co-cultivation, explants are transferred to hormone-free Murashige/Skoog medium (1×MS salts, 3% sucrose, 0.7% phytagar, pH 5.7) and 150 mg/ml timentin to eliminate *Agrobacterium*. Alternatively, explants could be transferred to hormone-restricted media containing auxin (e.g. NAA at 0.1 mg/l) or cytokinin (e.g. BAP at 0.1 g/l) at levels that do not promote the regeneration of untransformed shoots. Shoots are evident 4-6 weeks after infection. Only one shoot with a normal appearance was excised from each hypocotyl explant to ensure that replicates of a single transformation event were not taken.

Table 3 shows the results of phenotypic and PCR analysis. Two tobacco trials demonstrated that, on average, 13% of normal-looking (having apical dominance, not shooty) regenerated shoots were positive for the transgene of interest and negative for backbone.

The method can be applied to other *Solanaceous* plant species including pepper, eggplant, *Solanum phureja*, and petunia.

Example 5

Production of Transformed and Backbone-free Canola Plants Containing Test Constructs Internode segments roughly 6-12 mm long are cut from healthy and actively growing, aseptic canola plants (*Brassica napus* cv. Westar). As a source of aseptic stock plants, rooted seedlings should be grown for 4 to 6 week on 0.5×MS medium, 1.5% sucrose and solidified with gelrite. It was determined that hypocotyl explants are not adequate for the method described in the invention as they only form roots on MS medium without plant hormones. Cotyledon petiole explants are also prone to rooting and poor regeneration on hormone-free regeneration medium. Disarmed *Agrobacterium tumefaciens* strains (such as LBA4404) are used to deliver the P-DNA containing the gene of interest nptII and backbone containing the ipt gene driven by the Ubiquitin-7 promoter into the cells of the internodal explants of canola. After co-cultivation, explants are transferred to hormone-free Murashige/Skoog medium (1×MS salts, 3% sucrose, 0.7% phytagar, pH 5.7) and 150 mg/ml timentin to eliminate *Agrobacterium*. Alternatively, explants can be transferred to media containing auxin (e.g. NAA at 0.1 mg/l) or cytokinin (e.g. zeatin riboside at 0.2 g/l) at levels that will not promote the regeneration of untransformed shoots. Depending on the condition of the explant material and growing conditions, explants begin to form shoots after about a months time and continue coming for up to 4 more weeks. Only one shoot with a normal appearance was excised from each hypocotyl explant to ensure that replicates of a single transformation event were not taken.

Table 4 shows the results of phenotypic and PCR analysis. Two experiments demonstrated that, on average, 3% of regenerated, normal-looking (having apical dominance, not shooty) shoots were positive for the transgene of interest and negative for backbone.

The method can also be applied to other *Brassica* species.

Example 6

Production of Transformed and Backbone-free Apple Plants Containing Test Constructs

*Malus×domestica* cv. Golden Delicious plants are maintained in vitro on shoot proliferation medium (MS salts, 5 uM BAP and 0.7% agar). Shoot cultures are kept at 25 C with a 16:8 h photoperiod. Young, expanding leaves of 3-week-old shoot cultures are collected into sterile water and cut into 3-4 segments perpendicular to the midrib. Leaf explants are mixed with an *Agrobacterium* suspension at $OD_{600}$=0.2 for 10 minutes. Leaf segments are blotted on sterile filter paper to remove excess bacterial cells and co-cultivated on co-cultivation medium (MS basal medium, 3 uM thidiazuron (TDZ), 5 uM NAA, 0.2% gelrite) with adaxial surface up. After 2 days, explants are transferred to MS medium with 150 mg/l timentin and solidified with agar (0.7%). In this case, hormone-free medium was used. Alternatively, explants could be transferred to medium containing auxin (e.g. NAA at 5 uM) or cytokinin (e.g. TDZ at 0.03 uM) at levels that will not promote the regeneration untransformed shoots but could improve regeneration of shoots impacted by ipt overexpression. Explants are transferred to fresh MS hormone-free or hormone-poor medium every 2-4 weeks. For the initial 2 week period, the cultures are kept in the dark at 24 C then moved to light. Green, normal looking shoots (not showing ipt positive phenotype) are transferred to hormone-free, MS medium with 50 mg/l kanamycin to screen for the presence of the gene of interest. Surviving, gene-of-interest positive shoots are transferred to proliferation medium after 4 weeks on screening medium. Samples are collected for molecular confirmation.

The method can also be applied to transform other fruit trees including pear, cherrie, and plum.

Example 7

Use of Hormone-restricted Media

As described, it is possible to add small amounts of hormones to media. These amounts are generally not sufficient to induce shoot formation in non-infected explants. Broccoli (cv. Green Comet) explants are infected with disarmed *Agrobacterium tumefaciens* strains that deliver the P-DNA containing the gene of interest nptII and backbone containing the ipt gene into the cells. Explants are 5×5 mm sections of young leaves cut from 5-week-old plants maintained in vitro. After a two-day co-culture the explants are transferred to Murashige/Skoog medium (1×MS salts, 1× Gamborgs Vitamins, 3% sucrose, 0.7% phytagar, pH 5.7, 150 mg/ml timentin) supplemented with 0.5, 1, 2 or 4 mg/l of NAA. Plates are kept at 25 C with a 16/8 h photoperiod. After one month explants were transferred to new medium of the same make-up. Only one shoot with a normal appearance was excised from each hypocotyl explant to ensure that replicates of a single transformation event were not taken. Green, normal looking shoots (not showing ipt positive phenotype) are transferred to hormone-free, MS medium with 25 mg/l kanamycin to screen for the presence of the gene of interest. Surviving, gene-of-interest positive shoots are transferred to MS medium without kanamycin and solidified with agar after 4 weeks on screening medium. Samples are collected for molecular confirmation.

The combination of the cytokinin produced by the ipt gene and exogenously applied NAA creates marker-free, backbone-free transgenics or intragenics.

Example 8

Employment of Alternative Hormone Genes

Here is demonstrated the use of a single binary with the Baby Boom AP2/ERF transcription factor (BBM) gene in the backbone and the gene of interest in the P-DNA to generate marker-free, backbone-free plants. The construct contains the gene of interest nptII, within P-DNA left and right borders driven by a constitutive promoter expressed in the callus and developing plantlet (e.g. Ubiquitin-7 promoter) terminated by the 3'-termination sequence of the ubiquitin-3 gene. Within the backbone of the same binary is inserted the BBM gene by the ubiquitin promoter and terminated by the 3'-termination sequence of the ubiquitin-3 gene. The hormone biosynthetic gene cassette is placed close to the left border sequence (240 base pairs of backbone sequence separate the ubiquitin-3 terminator from the start of the left border). Disarmed *Agrobacterium tumefaciens* strains (such as LBA4404) are used to deliver the P-DNA into the cells of the internodal explants of potato. Ten fold dilutions of overnight cultures of *Agrobacterium* were grown for 5 to 6 hours. This culture was precipitated at 2800 rpm, washed with MS liquid medium (1×MS salts, 3% sucrose, pH 5.7) and resuspended in the same to make a 0.2 OD600. Co-cultivation of *Agrobacterium* with potato explants occurred on co-culture medium (0.1×MS salts, 3% sucrose, 0.7% phytagar, pH 5.7) for 2 days. After co-cultivation, explants are transferred to hormone-free Murashige/Skoog medium (1×MS salts, 3% sucrose, 0.7% phytagar, pH 5.7) and 150 mg/ml timentin to eliminate *Agrobacterium*. Alternatively, explants can be transferred to media containing auxin (e.g. NAA at 0.1 mg/l) or cytokinin (e.g. zeatin riboside at 0.25 g/l) at levels that will generally not promote the regeneration of untransformed shoots. After one month explants are transferred to new medium of the same make-up. Plantlets arising from transformation events where the vector sequences including BBM are stably integrated have an abnormal phenotype. Dwarfed plantlets with reduced apical dominance and rumpled leaves with wavy margins are ignored. One normal looking shoot is excised from each explant that provides one. A tissue sample is taken for PCR analysis to verify the presence of the gene of interest and the absence of backbone sequences.

It is also possible to combine more than one cytokinin synthesis gene into the same binary backbone or to combine a cytokinin gene together with an auxin synthesis gene.

Example 9

Marker-free and Backbone-free all Native DNA Transformation

The above examples demonstrate the utility of placing a plant biosynthetic gene or genes in the backbone of the vector harboring the gene of interest within the P-DNA to generate marker free transgenics. A complex construct carrying two large inverted repeats (FIG. 3) is placed between P-DNA borders. Within the backbone of the same binary is inserted the cytokinin biosynthetic gene ipt driven by the ubiquitin promoter and terminated by the 3'-termination sequence of the ubiquitin-3 gene. Ten fold dilutions of overnight cultures of the *Agrobacterium* harboring this vector were grown for 5 to 6 hours. This culture was precipitated at 2800 rpm, washed with MS liquid medium (1×MS salts, 3% sucrose, pH 5.7) and resuspended in the same to make a 0.2 OD600. Co-cultivation of *Agrobacterium* with 21,000 Russet Ranger potato explants occurred on co-culture medium (0.1×MS salts, 3% sucrose, 0.7% phytagar, pH 5.7) for 2 days. After co-cultivation, explants are transferred to hormone-poor Murashige/Skoog medium (1×MS salts, 3% sucrose, 0.7% phytagar, pH 5.7) and 150 mg/ml timentin to eliminate *Agrobacterium*. Alternatively, explants can be transferred to media containing auxin (e.g. NAA at 0.1 mg/l) or cytokinin (e.g. zeatin riboside at 0.25 g/l) at levels that do not promote the regeneration of untransformed shoots. After one month explants were transferred to new medium of the same make-up. Shoots begin to arise in about one and a half months. During the second month and third months, normal looking shoots are excised from explants. Nearly 65% of all explants formed normal-looking shoots after 3 months on hormone poor medium. Shoots with normal phenotypes are observed to root on MS medium without hormones and do not have a branching, multiple shoot and chlorotic appearance.

A PCR based method is used to score plants for the presence or absence of P-DNA and vector backbone sequences. Of the 6,500 normal-looking shoots scored by PCR, 65 (1%) were positive for the gene of interest and lacked backbone DNA. These results show that even extremely complex transfer DNAs can be effectively introduced into plants using the marker-free and backbone-free transformation method.

Tables

TABLE 1

Experimental results for frequency of marker-free and backbone free events in the Solanaceous crop potato (*Solanum tuberosum* cvs. Russet Ranger and Bintje)

| Cultivar | No. explants infected | No. normal shoots sampled* | No. events with gene of interest & no backbone |
|---|---|---|---|
| Bintje | 250 | 100 | 6 |
|  | 250 | 100 | 5 |
|  | 250 | 100 | 5 |
| Ranger | 250 | 100 | 10 |
|  | 250 | 100 | 5 |
|  | 250 | 100 | 5 |

*Normal shoots are those that do not have an ipt-induced phenotype. Ipt-positive shoots are chlorotic, shooty, lack apical dominance and do not root or root only poorly on hormone-free MS media.

TABLE 2

Experimental results for frequency of marker-free and backbone free events in the Solanaceous crop tomato (*Lycopersicum esculentum* cv. MoneyMaker)

| Cultivar | No. explants infected | No. normal shoots sampled* | No. events with gene of interest & no backbone |
|---|---|---|---|
| MoneyMaker | 294 | 42 | 1 |
|  | 286 | 60 | 1 |

*Normal shoots are those that do not have an ipt-induced phenotype. Ipt-positive shoots are chlorotic, shooty, lack apical dominance and do not root or root only poorly on hormone-free MS media.

TABLE 3

Experimental results for frequency of marker-free and backbone free events in the Solanaceous crop tobacco (*Nicotiana tabacum* cv. Petite Havana)

| Cultivar | No. explants infected | No. normal shoots sampled* | No. events with gene of interest & no backbone |
|---|---|---|---|
| Petite | 100 | 88 | NA |
| Havana | 100 | 62 | NA |

NA = data not available
*Normal shoots are those that do not have an ipt-induced phenotype. Ipt-positive shoots are chlorotic, shooty, lack apical dominance and do not root or root only poorly on hormone-free MS media.

TABLE 4

Experimental results for frequency of marker-free and backbone free events in the Cruciferous crop canola (*Brassica napus* cv. Westar)

| Cultivar | No. explants infected | No. normal shoots sampled* | No. events with gene of interest & no backbone |
|---|---|---|---|
| Westar | 146 | 46 | 1 |
|  | 68 | 20 | 1 |

*Normal shoots are those that do not have an ipt-induced phenotype. Ipt-positive shoots are chlorotic, shooty, lack apical dominance and do not root or root only poorly on hormone-free MS media.

What is claimed is:

1. A method for producing a transformed plant that does not contain a selectable marker in its genome, comprising (a) infecting plant cells with *Agrobacterium* containing a plasmid that comprises (i) a transfer-DNA that does not contain a selectable marker gene and (ii) an expression cassette, positioned outside of the transfer-DNA, for expressing a cytokinin biosynthetic gene; (b) culturing the cells on a hormone-free medium to produce shoots, or on medium which contains an amount of hormone that does not promote the regeneration of untransformed shoots but does improve regeneration of shoots produced through cytokinin biosynthetic gene expression; (c) identifying a shoot that has genomic DNA containing the transfer-DNA but not the cytokinin biosynthetic gene expression cassette; and (d) growing a plant from the identified shoot of (c), wherein the plant is a transformed plant that does not contain a selectable marker in its genome.

2. The method of claim 1, wherein the cytokinin biosynthetic gene is selected from the group consisting of an isopentenyl transferase gene, a cytokinin-independent 1 (CDK-1) gene, an ESR-2 gene, an ESR-1A gene, and a Sho gene.

3. The method of claim 1, wherein the expression of a nucleic acid sequence in the transfer-DNA modifies a trait in the resultant transgenic plant, wherein the trait is at least one of (i) lower levels of acrylamide, (ii) reduced black-spot bruising, and (iii) reduced cold-induced sweetening in comparison to a plant that does not comprise a cell that expresses that nucleic acid sequence.

4. The method of claim 1, wherein the transfer-DNA comprises nucleic acid sequences that are native to the genome of the plant cell.

5. A method for producing a transformed plant that does not contain a selectable marker in its genome, comprising (a) infecting plant cells with *Agrobacterium* containing a plasmid that comprises (i) a transfer-DNA that does not contain a selectable marker gene and (ii) an expression cassette, positioned outside of the transfer-DNA, for expressing a cytokinin biosynthetic gene; (b) culturing the transformed cells on either hormone-free medium to produce shoots, or on medium which contains an amount of hormone that does not promote the regeneration of untransformed shoots but does improve regeneration of shoots produced through cytokinin biosynthetic gene expression; (c) growing the shoots into plants; and (d) identifying a plant that has genomic DNA that contains the transfer-DNA but not the cytokinin biosynthetic gene, wherein the plant of (d) is a transformed plant that does not contain a selectable marker in its genome.

6. The method of claim 1, wherein the medium comprises auxin, cytokinin, or thidiazuron at a concentration that does not promote the regeneration of untransformed shoots.

7. The method of claim 6, wherein the auxin is 1-naphthaleneacetic acid (NAA) or indole-3-acetic acid (IAA).

8. The method of claim 7, wherein the concentration of NAA or IAA is 0.5, 1, 2 or 4 mg/l.

9. The method of claim 6, wherein the cytokinin is zeatin riboside or 6-benzylaminopurine (BAP).

10. The method of claim 9, wherein the concentration of zeatin riboside or BAP is 0.1, 0.2 or 0.25 mg/l.

11. The method of claim 6, wherein the concentration of thidiazuron is about 0.03 uM.

12. The method of claim 6, wherein the medium is a co-cultivation medium comprising thidiazuron and NAA.

13. The method of claim 12, wherein the concentration of thidiazuron is about 3 uM and the concentration of NAA is about 5 uM.

14. The method of claim 1, wherein the plant cells of step (a) are in an explant.

15. The method of claim 5, wherein the plant cells of step (a) are in an explant.

16. The method of claim 5, wherein the cytokinin biosynthetic gene is selected from the group consisting of an isopentyl transferase gene, a cytokinin-independent 1 gene, an ESR-2 gene, an ESR-1A gene, and a Sho gene.

17. The method of claim 1, wherein the plant cells are from a dicotyledonous plant.

18. The method of claim 17, wherein the dicotyledonous plant is selected from the group consisting of potato, tobacco, tomato, eggplant, petunia, sugarbeet, broccoli, cabbage, cauliflower, cassava, canola, sweet potato, pepper, cotton, poinsettia, legumes, alfalfa, soybean, carrot, strawberry, lettuce, melon, oak, maple, walnut, rose, mint, squash, chrysanthemum, apple, pear, cherry, plum, sunflower, safflower, and cactus.

19. The method of claim 5, wherein the plant cells are from a dicotyledonous plant.

20. A method for producing a transformed plant that does not contain a selectable marker in its genome, comprising (a) infecting plant cells with *Agrobacterium* containing a plasmid that comprises (i) a transfer-DNA that does not contain a selectable marker gene and (ii) an expression cassette, positioned outside of the transfer-DNA, for expressing a cytokinin biosynthetic gene; (b) culturing the transformed cells on either hormone-free medium to produce shoots, or on medium which contains an amount of hormone that does not promote the regeneration of untransformed shoots but does improve regeneration of shoots produced through plant hormone biosynthetic gene expression, wherein the medium comprises 1-naphthaleneacetic acid (NAA) or indole-3-acetic acid (IAA); (c) growing the shoots into plants; and (d) identifying a plant that has genomic DNA that contains the transfer-DNA but not the plant hormone biosynthetic gene, wherein the plant of (d) is a transformed plant that does not contain a selectable marker in its genome.

21. The method of claim 20, wherein the concentration of NAA or IAA is 0.5, 1, 2 or 4 mg/l.

* * * * *